US012168029B2

(12) United States Patent
Zahalsky

(10) Patent No.: US 12,168,029 B2
(45) Date of Patent: *Dec. 17, 2024

(54) METHODS AND COMPOSITIONS FOR TREATMENT OF PENILE DEFECTS

(71) Applicant: Michael P. Zahalsky, Parkland, FL (US)

(72) Inventor: Michael P. Zahalsky, Parkland, FL (US)

( * ) Notice: Subject to any disclaimer, the term of this patent is extended or adjusted under 35 U.S.C. 154(b) by 987 days.

This patent is subject to a terminal disclaimer.

(21) Appl. No.: 17/103,248

(22) Filed: Nov. 24, 2020

(65) Prior Publication Data

US 2021/0077538 A1   Mar. 18, 2021

Related U.S. Application Data

(60) Continuation-in-part of application No. 16/711,673, filed on Dec. 12, 2019, now Pat. No. 11,160,835, and a continuation of application No. 15/541,988, filed on Jul. 6, 2017, now abandoned, said application No. 16/711,673 is a division of application No. 15/158,101, filed as application No. PCT/US2016/016934 on Feb. 8, 2016, now Pat. No.

(Continued)

(51) Int. Cl.
| | |
|---|---|
| A61K 35/48 | (2015.01) |
| A61K 9/00 | (2006.01) |
| A61K 31/568 | (2006.01) |
| A61K 35/16 | (2015.01) |
| A61K 35/28 | (2015.01) |
| A61K 35/35 | (2015.01) |
| A61K 35/50 | (2015.01) |
| A61K 35/545 | (2015.01) |
| A61K 38/09 | (2006.01) |
| A61K 38/18 | (2006.01) |
| A61K 38/24 | (2006.01) |
| A61K 38/27 | (2006.01) |
| A61K 38/39 | (2006.01) |
| A61K 38/48 | (2006.01) |
| A61K 45/06 | (2006.01) |
| A61K 47/42 | (2017.01) |
| A61L 27/22 | (2006.01) |
| A61L 27/24 | (2006.01) |
| A61L 27/36 | (2006.01) |
| A61L 27/38 | (2006.01) |
| A61L 27/54 | (2006.01) |
| A61L 27/58 | (2006.01) |
| C12N 5/00 | (2006.01) |
| C12N 5/071 | (2010.01) |
| C12N 5/0775 | (2010.01) |

(52) U.S. Cl.
CPC ............ A61K 35/48 (2013.01); A61K 9/0019 (2013.01); A61K 9/0024 (2013.01); A61K 9/0034 (2013.01); A61K 31/568 (2013.01); A61K 35/16 (2013.01); A61K 35/28 (2013.01); A61K 35/35 (2013.01); A61K 35/50 (2013.01); A61K 35/545 (2013.01); A61K 38/09 (2013.01); A61K 38/18 (2013.01); A61K 38/24 (2013.01); A61K 38/27 (2013.01); A61K 38/39 (2013.01); A61K 38/4886 (2013.01); A61K 45/06 (2013.01); A61K 47/42 (2013.01); A61L 27/225 (2013.01); A61L 27/24 (2013.01); A61L 27/3633 (2013.01); A61L 27/3834 (2013.01); A61L 27/54 (2013.01); A61L 27/58 (2013.01); C12N 5/00 (2013.01); C12N 5/0667 (2013.01); C12N 5/0683 (2013.01); A61L 2300/41 (2013.01); A61L 2300/414 (2013.01); A61L 2400/06 (2013.01)

(58) Field of Classification Search
None
See application file for complete search history.

(56) References Cited

U.S. PATENT DOCUMENTS

| | | | | |
|---|---|---|---|---|
| 2009/0311223 | A1* | 12/2009 | Ichim | A61K 35/36 514/1.1 |
| 2012/0156178 | A1* | 6/2012 | Borgos | A61P 15/00 424/94.67 |
| 2015/0335681 | A1* | 11/2015 | Chapman | A61L 27/3604 424/93.3 |

FOREIGN PATENT DOCUMENTS

WO   WO-2013116327 A1 *  8/2013   ........... A61K 31/568

OTHER PUBLICATIONS

Zhang et al., Stem cells: novel players in the treatment of erectile dysfunction, Asian Journal of Andrology, vol. 14, pp. 145-155 (Year: 2012).*

(Continued)

Primary Examiner — Michelle F. Paguio Frising
(74) Attorney, Agent, or Firm — David O. Simmons

(57) ABSTRACT

Compositions for use in treating penile defects, including erectile dysfunction and Peyronie's disease. Compositions include penile stem cells and isolated penile stem cells substantially free of red blood cells, additives such as amnion, amniotic fluid, extracellular matrix components, growth factors, anti-inflammatories, antioxidants, wound healing agents, and collagenases. Also provided are methods of treating said penile defects in a patient, including implanting a composition of penile stem cells or platelet rich plasma derived from the penis into a patient. Methods include implanting a composition of amnion and/or amniotic fluid into a patient for a penile defect. Also provided are methods of isolating penile stem cells substantially free of red blood cells by providing a whole blood specimen obtained from the penis of a subject; separating the whole blood into fractions containing penile stem cells and the red blood cells from the specimen; and collecting the penile stem cell fraction.

9 Claims, No Drawings

Related U.S. Application Data 10,548,925, said application No. 15/158,101 is a division of application No. 14/363,142, filed as application No. PCT/US2013/023830 on Jan. 30, 2013, now Pat. No. 10,751,374.

(60) Provisional application No. 61/592,108, filed on Jan. 30, 2012.

(56) References Cited

OTHER PUBLICATIONS

Silini et al., "Soluble Factors of Amnion-Derived Cells in Treatment of Inflammatory and Fibrotic Pathologies", Current Stem Cell Research & Therapy, vol. 8, pp. 6-14 (Year: 2013).*
Chun et al., "Human Amniotic Fluid Stem Cell-derived Muscle Progenitor Cell Therapy for Stress Urinary Incontinence", Journal of Korean Medical Science, vol. 27, pp. 1300-1307 (Year: 2012).*

* cited by examiner

METHODS AND COMPOSITIONS FOR TREATMENT OF PENILE DEFECTS

RELATED APPLICATIONS

This application is a continuation of co-pending U.S. application Ser. No. 15/541,988 filed on Jul. 6, 2017 which is the United States national phase of International Application No. PCT/US2016/016934 filed Feb. 8, 2016 and claims priority to U.S. Provisional Application No. 62/112,709 filed Feb. 6, 2015; and a continuation in part of co-pending U.S. application Ser. No. 16/711,673 filed on Dec. 12, 2019 which is a division of U.S. application Ser. No. 15/158,101 filed on May 18, 2016 now U.S. Pat. No. 10,548,925 which is a division of U.S. application Ser. No. 14/363,142 filed on Jun. 5, 2014 now U.S. Pat. No. 10,751,374, which is the United States national phase of International Application No. PCT/US2013/023830 filed Jan. 30, 2013 and claims priority to U.S. Provisional Application No. 61/592,108 filed Jan. 30, 2012, the disclosures of which are hereby incorporated in their entirety by reference.

TECHNICAL FIELD

The present invention relates to compositions for use in medical procedures, methods for use thereof, and methods of preparation thereof. More specifically, the invention relates to compositions including stem cells, such as penile stem cells, useful for regenerating tissue, improving vasculogenesis and angiogenesis in disease and improving wound healing, specifically in penile disease and defects.

BACKGROUND OF THE INVENTION

Use of stem cells has grown exponentially over the past two decades as methods of isolating and purifying these cells has become simpler and more cost-effective. In particular, with the advent of the ability to obtain adult stem cells, as opposed to politically-charged embryonic stem cells, work in the field has blossomed. Stem cells have been suggested as a cure for ailments ranging from Parkinson's disease (replacing dying dopaminergic cells of the substantia nigra) to myocardial infarctions and cardiomyopathy. Gimble J M et al. Adipose-derived stem cells for regenerative medicine. Circulation Res. 2007; 100: 1249-1260; Kondo K et al. Implantation of adipose-derived regenerative cells enhances ischemia-induced angiogenesis. Arteriosclerosis, Thrombosis, and Vascular Biol. 2009; 29: 61-66.

Other defects and diseases may also be candidates for stem cell intervention. One area of interest is that of penile defects, such as erectile dysfunction (ED) and Peyronie's disease. At least some forms of ED trace their etiology to vascular deficits in the penile tissue. Pharmaceutical compositions for treating ED do exist; however, a need exists for a treatment that does not require use of medicaments. At least one group has reported success in the use of stem cells derived from bone marrow to reverse ED in an animal model. Kendirci M et al. Transplantation of non-hematopoietic adult bone marrow stem/progenitor cells isolated by the p75 nerve growth factor receptor into the penis rescues ED in a rat model of cavernous nerve injury. J. Urol. 2010; 184(4): 1560-1566. Another group has seen success in using muscle-derived stem cells in a rat model of ED. Woo J C et al. Transplantation of muscle-derived stem cells into the corpus cavernosum restores erectile function in a rat model of cavernous nerve injury. Korean J. Urol. 2011; 52: 359-363.

Peyronie's disease is an ailment involving the growth of fibrous plaques in the soft tissue of the penis. These plaques grow in the tunica albuginea, a region of connective tissue that is part of the more general connective tissue of Buck's fascia. The tunica albuginea is an area surrounding the corpora cavernosa. The disease results in pain, ED, and alteration of penis shape, and may be caused by disorganized collagen fibers. Treatments for the disease currently include administration of corticosteroids to the plaques, radiation therapy, and vitamin E. Pharmaceuticals for treatment exist; however, the use of medicaments is considered controversial in the art, and these compounds have not met with sustained success. Hauck E W et al. A critical analysis of nonsurgical treatment of Peyronie's disease. European Urology 2006; 49(6): 987-97. The newest medication is Clostridium Histolyticum Collagenase which has potentially harmful side effects.

In light of the above, a need exists in the art for compositions, such as compositions of stem cells, that are easy to obtain and isolate, methods for obtaining such stem cells, and methods for using stem cells in treating penile defects.

SUMMARY OF THE INVENTION

In one aspect, provided herein are compositions that comprise a population of isolated penile stem cells substantially free of red blood cells. In some embodiments, the penile stem cells are derived from a donor. In some embodiments, the penile stem cell is mixed with amniotic fluid.

In another aspect, provided herein are compositions that comprise adipose tissue and isolated stem cells. In some embodiments, the isolated stem cells are a population of isolated penile stem cells substantially free of red blood cells. In some embodiments, the penile stem cell is derived from a donor, either alive or dead, such as a cadaver. In some embodiments, the isolated stem cells include stem cells placental or embryonic in origin. In other embodiments, the isolated stem cells include mesenchymal stem cells. In certain embodiments, the isolated stem cells include adipose-derived stem and regenerative cells (ADRC). In further embodiments, the stem cells and adipose tissue are derived from a donor.

In additional embodiments, the compositions include at least one additional additive. The additive may be a compound useful in wound healing, in decreasing inflammation, in breaking down collagen, or in promoting angiogenesis and/or vasculogenesis. In further embodiments, the compositions include a growth scaffold. In some embodiments, the penile stem cells are mixed with amnion and/or amniotic fluid, or growth factors, or testosterone, or human chorionic gonadotropin (HCG), or human growth hormone (HGH) or a combination thereof.

In another aspect, provided herein are methods of treating a penile defect in a subject, comprising providing a composition that includes a population of isolated penile stem cells, and implanting the composition within the penis of the subject. In some embodiments, the penile stem cells are derived from the subject. In some embodiments, the penile stem cells are mixed with amnion and/or amniotic fluid. In certain embodiments, the compositions comprise adipose tissue and stem cells, preferably penile stem cells that are derived from the subject. In some embodiments, the compositions include stem cells placental or embryonic in origin. In other embodiments, the penile stem cells are mesenchymal stem cells. In certain further embodiments, the compositions include ADRC. In further embodiments, the adipose tissue and ADRC are derived from the subject. In some embodiments, the composition is implanted into the subject's penis. In further embodiments, the composition is implanted into or around the subject's corpus cavernosum. In another embodiment, the composition is implanted into or around the subject's tunica albuginea. In certain embodiments the composition is injected into the tissue of interest. In other embodiments the composition is injected or infused into any artery that feeds penile tissue. In certain embodiments, the composition is injected or infused into the corporal arteries or internal pudendal arteries.

In another aspect, provided herein are methods of treating a penile defect in a subject, comprising providing a composition that includes amnion and/or amniotic fluid, and implanting the composition within the penis of the subject. In some embodiments, the compositions include stem cells placental or embryonic in origin. In other embodiments, the penile stem cells are mesenchymal stem cells. In some embodiments, the composition is implanted into the subject's penis. In further embodiments, the composition is implanted into or around the subject's corpus cavernosum. In another embodiment, the composition is implanted into or around the subject's tunica albuginea. In certain embodiments the composition is injected into the tissue of interest. In other embodiments the composition is injected or infused into any artery that feeds penile tissue. In certain embodiments, the composition is injected or infused into the corporal arteries or internal pudendal arteries.

In additional embodiments, the compositions that are implanted include at least one additional additive. The additive may be a compound useful in wound healing, in decreasing inflammation, in breaking down collagen, or in promoting angiogenesis and/or vasculogenesis. In further embodiments the composition includes an implantable or injectable growth scaffold, or a viscosity or scaffold that allows for a time-release or delayed release mechanism of action.

The present invention also provides methods of treating Peyronie's disease, erectile dysfunction or penile trauma by injecting a composition comprising at least one penile stem cell, at least one component of extracellular matrix, and at least one growth factor, and injecting that composition into the tunica albuginea or corpora cavernosum of a subject in need of treatment. The present invention also provides methods of treating Peyronie's disease, erectile dysfunction or penile trauma by injecting a composition comprising amnion and/or amniotic fluid, at least one component of extracellular matrix, and at least one growth factor, and injecting that composition into the tunica albuginea or corpora cavernosum of a subject in need of treatment.

In another aspect, provided herein are methods of obtaining penile stem cells substantially free of red blood cells, the methods comprising the steps of: providing a whole blood specimen obtained from the penis of a subject; separating the whole blood into fractions, wherein one fraction contains penile stem cells and a second fraction containing substantially all of the red blood cells from the specimen; and collecting the fraction containing the penile stem cells.

Other features and advantages of the present invention will become apparent from the following detailed description and examples. It should be understood, however, that the detailed description and the specific examples while indicating preferred embodiments of the invention are given by way of illustration only, since various changes and modifications within the spirit and scope of the invention will become apparent to those skilled in the art from this detailed description.

DESCRIPTION OF THE PREFERRED EMBODIMENTS

In one aspect, provided herein are compositions that comprise a population of isolated penile stem cells substantially free of red blood cells. In some embodiments, the penile stem cells are derived from a donor or cadaver. In some embodiments, the penile stem cell is mixed with amniotic fluid. In some embodiments, the cells are cultured and grown and then reinjected.

In another aspect, provided herein are compositions that comprise adipose tissue and isolated stem cells. In some embodiments, the isolated stem cells are a population of isolated penile stem cells substantially free of red blood cells. In some embodiments, the penile stem cell is derived from a donor or cadaver. In some embodiments, the isolated stem cells include stem cells placental or embryonic in origin. In other embodiments, the isolated stem cells include mesenchymal stem cells. In certain embodiments, the isolated stem cells include adipose-derived stem and regenerative cells (ADRC). In further embodiments, the stem cells and adipose tissue are derived from a donor.

In additional embodiments, the compositions include at least one additional additive. The additive may be a compound useful in wound healing, in decreasing inflammation, in breaking down collagen, or in promoting angiogenesis and/or vasculogenesis. In further embodiments, the compositions include a growth scaffold or a viscosity or scaffold that allows for a time-release or delayed release mechanism of action. In some embodiments, the penile stem cell is mixed with amniotic fluid.

In another aspect, provided herein are methods of treating a penile defect in a subject, comprising providing a composition that includes a population of isolated penile stem cells, and implanting the composition within the penis of the subject. In some embodiments, the penile stem cells are derived from the subject. In some embodiments, the penile stem cells are mixed with amnion and/or amniotic fluid. In certain embodiments, the compositions comprise adipose tissue and stem cells, preferably penile stem cells that are derived from the subject. In some embodiments, the compositions include stem cells placental or embryonic in origin. In other embodiments, the penile stem cells are mesenchymal stem cells. In certain further embodiments, the compositions include ADRC. In further embodiments, the adipose tissue and ADRC are derived from the subject. In some embodiments, the composition is implanted into the subject's penis. In further embodiments, the composition is implanted into or around the subject's corpus cavernosum. In another embodiment, the composition is implanted into or around the subject's tunica albuginea. In certain embodiments the composition is injected into the tissue of interest. In other embodiments the composition is injected or infused into any artery that feeds penile tissue. In certain embodiments, the composition is injected or infused into the corporal arteries or internal pudendal arteries.

In another aspect, provided herein are methods of treating a penile defect in a subject, comprising providing a composition that includes amnion and/or amniotic fluid, and implanting the composition within the penis of the subject. In some embodiments, the compositions include stem cells placental or embryonic in origin. In other embodiments, the penile stem cells are mesenchymal stem cells. In some embodiments, the composition is implanted into the subject's penis. In further embodiments, the composition is implanted into or around the subject's corpus cavernosum. In another embodiment, the composition is implanted into or around the subject's tunica albuginea. In certain embodiments the composition is injected into the tissue of interest. In other embodiments the composition is injected or infused into any artery that feeds penile tissue. In certain embodiments, the composition is injected or infused into the corporal arteries or internal pudendal arteries.

In additional embodiments, the compositions that are implanted include at least one additional additive. The additive may be a compound useful in wound healing, in decreasing inflammation, in breaking down collagen, or in promoting angiogenesis and/or vasculogenesis. In further embodiments the composition includes an implantable or injectable growth scaffold, or a viscosity or scaffold that allows for a time-release or delayed release mechanism of action.

The present invention also provides methods of treating Peyronie's disease, erectile dysfunction or penile trauma by injecting a composition comprising at least one penile stem cell, at least one component of extracellular matrix, and at least one growth factor, and injecting that composition into the tunica albuginea or corpora cavernosum of a subject in need of treatment. The present invention also provides methods of treating Peyronie's disease, erectile dysfunction or penile trauma by injecting a composition comprising amnion and/or amniotic fluid, at least one component of extracellular matrix, and at least one growth factor, and injecting that composition into the tunica albuginea or corpora cavernosum of a subject in need of treatment. In some embodiments, the extracellular matrix component(s) and/or growth factor(s) are placental or embryonic, amniotic or chorionic, or cadaveric in origin.

In another aspect, provided herein are methods of obtaining penile stem cells substantially free of red blood cells, the methods comprising the steps of: providing a whole blood specimen obtained from the penis of a subject; separating the whole blood into fractions, wherein one fraction contains penile stem cells and a second fraction containing substantially all of the red blood cells from the specimen; and collecting the fraction containing the penile stem cells.

In some embodiments, the stem cells are penile stem cells derived from the subject. In some embodiments, the penile stem cell is mixed with amniotic fluid. In certain embodiments, the composition comprises adipose tissue and stem cells, preferably penile stem cells, which may be derived from the subject. In some embodiments, the compositions include one or more additional types of stem cells. In some embodiments, the additional types of stem cells are placental or embryonic in origin. In other embodiments, the additional types of stem cells are mesenchymal stem cell. In certain further embodiments, the additional types of stem cells are ADRCs In further embodiments, the adipose tissue and ADRC are derived from the subject. In some embodiments, the composition is implanted into the subject's penis. In further embodiments, the composition is implanted into or around the subject's corpus cavernosum. In another embodiment, the composition is implanted into or around the subject's tunica albuginea. In certain embodiments the composition is injected into the tissue of interest. In other embodiments the composition is injected or infused into any artery that feeds penile tissue. In certain embodiments, the composition is injected or infused into the corporal arteries or internal pudendal arteries.

In additional embodiments, the composition that is implanted includes at least one additional additive or is only an additive of growth factors such as amniotic fluid. The additive may be a compound useful in wound healing, in decreasing inflammation, in breaking down collagen, or in promoting angiogenesis and/or vasculogenesis. In further embodiments the composition includes an implantable or injectable growth scaffold.

Penile stem cells may be used to advantageously promote vasculogenesis and wound healing in penile defects. These properties function to address defects and diseases such as ED. Additionally, penile stem cells may be provided directly to plaques in Peyronie's disease, stimulating wound healing. Penile stem cells are preferable for stem cell derived treatments of these defects because of their ability to stimulate vasculogenesis and to produce organized collagen.

In some embodiments, a composition of the present invention includes testosterone.

In some embodiments, a composition of the present invention includes human chorionic gonadotropin (hCG).

In some embodiments, a composition of the present invention includes human growth hormone (HGH) or somatropin.

In some embodiments, a composition of the present invention includes collagen.

Definitions

For convenience, certain terms employed in the entire application (including the specification, examples, and appended claims) are collected here. Unless defined otherwise, all technical and scientific terms used herein have the same meaning as commonly understood by one of ordinary skill in the art to which this invention belongs.

It is to be understood that this invention is not limited to the particular methodology, protocols, cell lines or type of stem cell, constructs, additives, and reagents described herein. It is also to be understood that the terminology used herein is for the purpose of describing particular embodiments only, and is not intended to limit the scope of the present invention which will be limited only by the appended claims.

The term "stem cell" refers to any multipotent or pluripotent cell, traditional stem cells, progenitor cells, preprogenitor cells, and reserve cells. These cells include Mesenchymal Stem Cells, Hematopoietic Stem Cells, Endothelial Stem Cells, and Pericytes. The term is used interchangeably with and may mean progenitor cell. A stem cell may be derived from an adult organism or from a cell line, or from an embryonic organism. Exemplary stem cells include embryonic stem cells, adult stem cells, pluripotent stem cells, neural stem cells, liver stem cells, muscle stem cells, muscle precursor stem cells, endothelial progenitor cells, bone marrow stem cells, chondrogenic stem cells, lymphoid stem cells, mesenchymal stem cells, hematopoietic stem cells, and the like. Descriptions of stem cells, including method for isolating and culturing them, may be found in, among other places, Embryonic Stem Cells, Methods and Protocols, Turksen ed., Humana Press, 2002.

The term "adult" as used herein refers to any non-embryonic organism. For example the term "adult adipose-derived regenerative cell," refers to an adipose-derived regenerative cell, other than that obtained from an embryo.

The term "embryo" as used herein refers to any multicellular diploid eukaryote during development, until birth or hatching. The term "embryonic stem cell" refers to a pluripotent cell derived from the inner cell mass of a blastocyst.

The term "mesenchymal stem cell" refers to any multipotent stromal cell derived from, for example and without limitation, umbilical cord blood, adipose tissue, muscle, corneal stroma, and dental pulp that can differentiate into cells such as, including but not limited to, osteoblasts, chondrocytes, and adipocytes.

The term "adipose-derived regenerative cell" (ADRC) is used interchangeably with adipose stem cells (ASC) herein and refers to adult cells that originate from adipose tissue. ADRC are a heterologous population of cells comprising at least one of the following population of cells; adult stem cells, vascular endothelial cells, vascular smooth muscle cells, endothelial cells, mesenchymal stem cells, fibroblasts, pericytes and additional other cell types.

In some embodiments, ADRC refers to a substantially pure population of adipose-derived stem cells. ADRC can be easily harvested from adipose tissue and are substantially free of adipocytes and red blood cells and clonal populations of connective tissue stem cells. The stromal vascular fraction cells are substantially devoid of extracellular matrix material from adipose tissue. ADRC may also be referred to as adipose-derived stem/stromal cells (ASCs), adipose-derived adult stem (ADAS) cells, adipose-derived adult stromal cells, adipose-derived stromal cells, adipose stromal cells, adipose mesenchymal cells, adipose-derived mesenchymal stem cells, lipoblasts, pericytes, preadipocytes, and processed lipoaspirate cells.

The term "adipose" as used herein refers to any fat tissue from a subject. The terms "adipose" and "adipose tissue" are used interchangeably herein. The adipose tissue may be brown fat, white fat or yellow fat or white adipose tissue, derived from subcutaneous, omental/visceral, mammary, gonadal, or other adipose tissue site. The adipose tissue has adipocytes and stroma. Adipose tissue is found throughout the body of an animal. For example, in mammals, adipose tissue is present in the omentum, bone marrow, subcutaneous space, and surrounding most organs. Such cells may comprise a primary cell culture or an immortalized cell line. The adipose tissue may be from any organism having fat tissue.

Preferably, the adipose tissue is human; most preferably, the adipose tissue is derived from the individual in need of treatment for a penile defect. A convenient source of adipose tissue is from liposuction surgery, however, the source of adipose tissue or the method of isolation of adipose tissue is not critical to the invention, and acquisition of adipose tissue by any means may adequately provide tissue and stem cells for the present invention.

The term "tissue" as used herein is a broad term that is applied to any group of cells that perform specific functions, and includes in some instances whole organs and/or part of organs. A tissue need not form a layer, and thus encompasses a wide range of tissue, including adipose tissue derived from any source in an organism. Preferably, the tissue is derived from a mammal Most preferably, the tissue is derived from the individual in need of treatment for a penile defect.

The term "implant" as used herein refers to any method for transferring a population of cells or cell mass into a subject, including by surgical implantation (incision into the tissue of interest and deposition therein) and injection by a syringe, needle, cannula, or the like of any suitable gauge. An implant as used herein can comprise genetically modified cells, as well as cells differentiated from other cells, such as stem cells, progenitors, and the like, as well as adipose cells or tissue.

The term "corpus cavernosum" of the penis refers to one of a pair of sponge-like regions of erectile tissue which contain most of the blood in the penis during penile erection. Generally, the two corpus cavernosum and a corpus spongiosum are three expandable erectile tissues along the length of the penis which fill with blood during erection. The term "corpus" is used interchangeably herein with corporal, corporeal and corporic, which are terms used to describe tissues which are derived from the corpora cavernosum or which can be developed, differentiated, or altered by natural or artificial means into corpora cavernosum tissue. The term "cavernosum" is used interchangeably herein as cavernae, corporum, cavernosum, or cavernosorum penis, and refers to the caverns of corpora cavernosa (or one of the two corpus cavernosum) of the penis or the dilatable spaces within the corpus cavernosum of the penis, which fill with blood and become distended with erection.

The term "tunica albuginea" refers to the fibrous tissue covering, or enveloping, the corpora cavernosa of the penis. This tissue consists of elastin and collagen. The term "Bucks fascia" refers to the layer of fascia covering the penis, including the tunica albuginea.

The terms "subject" and "individual" are used interchangeably herein, and refer to an animal, for example a human, from whom stem cells, for example penile stem cells can be harvested, or a subject into whom tissue can be transplanted for treatment, for example treatment for penile defects, using the compositions and methods described herein. For treatment of conditions or disease states which are specific for a specific animal such as a human subject, the term "subject" refers to that specific animal. In some embodiments, the subject is a human subject. It is possible in embodiments of this invention that recipient subjects are of a different mammalian subject than the donor subject.

Compositions and Methods for Treating Penile Defects, Peyronie's Disease, Erectile Dysfunction One aspect of the present invention provides for compositions. The compositions comprise a population of isolated penile stem cells. The composition is one that is suitable for implantation into a subject, for example an animal, preferably a mammal. In a preferred embodiment, the composition is suitable for implantation into a human. In a further preferred embodiment, the at least one penile stem cell of the composition is suitable for implantation into a human because they are derived from the same human subject.

Another aspect of the present invention provides for a composition that comprises adipose tissue and a population of isolated stem cells, such as a penile stem cell. The composition is one that is suitable for implantation into a subject, for example an animal, preferably a mammal. In a preferred embodiment, the composition is suitable for implantation into a human. In a further preferred embodiment, the adipose tissue and at least one stem cell of the composition are suitable for implantation into a human because they are derived from the same human subject.

Stem cells include, but are not limited to, mesenchymal stem cells. The stem cells may be obtained from any suitable source, for example, and without limitation, stem cells may be obtained from adult or embryonic sources, from bone marrow, from placental tissue, from umbilical cord blood, and from adipose tissue. In preferred embodiments, the stem cell is obtained from adipose tissue, and is an adipose-derived regenerative cell (ADRC). In more preferred embodiments, the stem cell is obtained from the penis, and is a penile stem cell.

In general, adipose tissue may be collected in any suitable manner. For example, in embodiments, adipose tissue is obtained through dry liposuction, wet liposuction, super-wet liposuction, tumescent liposuction, power-assisted liposuction, laser-assisted liposuction, or the like.

Once harvested by any suitable method, adipose tissue may be processed by known methods. The following methods are to be considered exemplary. In a preferred embodiment, adipose tissue is processed using the STEM-SOURCE® Cellbank or Cytori Celution System. The Cytori procedure and system therefore are disclosed in detail in U.S. Pat. Nos. 7,501,115 and 7,687,059. Briefly, adipose tissue is harvested from a subject. In a preferred, embodiment of the current invention, the subject is an individual in need of treatment for a penile defect. The tissue is processed to remove mature adipocytes and connective tissue from the sample. Processing may occur within a system having a tissue collection port, filter disposed within the system, and a mixing container for holding the processed sample. The filter works to remove the unwanted cells and non-cellular materials from the sample, enriching the proportion of ADRCs in the filtered sample.

The Cytori system has successfully been used in providing ADRCs for breast tissue implantation for reconstruction after radical lumpectomy, proving the ability of stem cells isolated by this method to generate tissue of a single type (adipocytes, or fat). Similarly, in treatment of penile defects, only one type of tissue need be generated. As such, the Cytori method and system is well suited for use in preparing a composition of the current invention. With regard to use of the Cytori system and method itself, processing is accomplished by washing and disaggregating the tissue to reduce the presence of free lipids and blood elements. Processing may or may not also include a rinsing step; the step conducted using isotonic saline or any other suitable physiologic solution known to those skilled in the art.

Remaining tissue is then disaggregated using enzyme degradation or mechanical disaggregation. The cells and solution are then centrifuged to separate cells, including ADRC, from the degradation solution. The cells form a pellet in the centrifuge, and the pellet can be frozen for storage or resuspended in another solution, for example a buffer, for use in medical treatments such as those recited herein.

The concentration of stem cells obtained by this method may vary, but typically approximately 0.1% of the cells in the pellet are stem cells. Greater percentages may be obtained by varying the above method, for example by use of adherence protocols such as described in Berdel W E et al., Purification of human monocytes by adherence to polymeric fluorocarbon. Immunobiology 1982 163(5): 511-520, or by separation on the basis of cell-surface markers, for example on the basis of markers present on differentiated cells, such as CD34 and the like, or by selecting based on markers expressed on progenitor cells, such as CD90 and the like. In a preferred, embodiment, the percentage of stem cells present in the pellet is between approximately 2% and 12%.

For embodiments where the individual to be treated is not the donor of the adipose tissue and the population of isolated penile stem cells the composition may further comprise immunosuppressive agents designed to prevent rejection of the composition once implanted Immunosuppressive agents may be selected from glucocorticoids, cytostatics, antibodies, pharmaceuticals such as tacrolimus, ciclosporin, sirolimus, interferons, opioids, mycophenolic acid, fingolimod, and myriocin.

In other embodiments adipose tissue is derived from lipoaspirate (i.e. from liposuction), is washed, exposed to a collagenase digest at 37° Celsius, and centrifuged.

While specific penile stem cell isolation procedures are provided herein, the invention described should not be limited to those procedures. It should be apparent to those skilled in the art that other means of isolating stem cells, in particular penile stem cells, are possible and may be used interchangeably with the current invention. For example, penis stem cells can be isolated from tissue obtained from a biopsy of the penis by a variety of techniques, such as by using an 18 gauge needle biopsy gun. They can also be obtained via a trocar or needle by draining blood and fluid from an erect penis from the patient then processed, activated, and/or minimally manipulated and placed back into the subject's penis In some embodiments, penile stem cells may be isolated from a whole blood sample obtained from the penis of a subject by preparing and extracting the platelet rich plasma preparation, which contains the penile stem cells, from the specimen. This is a similar method used to obtaining bone marrow stem cells.

The U.S. Food and Drug Administration has approved two methods for platelet rich plasma (PRP) preparation. Both methods involve the collection of whole blood (with the anticoagulant citrate dextrose) and two stages of centrifugation designed to separate PRP from platelet-poor plasma and red blood cells.

Briefly, skin is prepared in a sterile manner for drawing blood. The blood is gently drawn or aspirated into an anticoagulated syringe, such as a 20 cc syringe. Care is taken to not activate the platelets or rupture the RBCs. The first spin separates red blood cells (RBC) from the PRP and the RBCs are discarded. The second spin concentrates platelets and white cells with the supernatant being platelet poor plasma (PPP), which is removed. The remaining plasma is used to resuspend the platelets and white cells. For about 60 cc of anticoagulated blood drawn and processed, about 10 cc of PRP is obtained.

In some embodiments, the PRP can be used directly for reinjection into the penis. In some embodiments, the PRP can also be added to or enriched with other types of stem cells, such as those discussed below. In other embodiments, the PRP is centrifuged and the penile stem cells pelleted and then resuspended in a suitable media. In some embodiments, PRP or penile stem cells are mixed with growth factors such as amnion or amniotic fluid or other biologic or non-biologic growth factors, such as platelet derived growth factor or endothelial derived growth factor or testosterone, human chorionic gonadotropin (hCG), human growth hormone (HGH) or somatropin. In some embodiments, the penile stem cells are mixed with Natural Killer (NK cells) harvested from the subject. In some embodiments, the penile stem cells are resuspended with PRP containing autologous growth factors. In some embodiments, the penile stem cells are resuspended in saline, such as phosphate-buffered saline (PBS). In some embodiments, the penile stem cells are resuspended with a buffer, for example bicarbonate for a basic composition or phosphate for an acidic composition. Without wishing to be bound by theory, the NK cells can dissolve Peyronie's plaques.

The penile stem cells and compositions described herein can be injected into the penile arteries or the urethral sphincter or layered on a flap externally or internally, or injected into a stricture or fistula or into the corpora cavernosum, bulbo spongiosum, or tunica albiginea or urethra. They can also be injected during open surgery for Peyronie's disease. In some embodiments, the penile stem cells and compositions described herein are administered in the form of a gel or putty. In some embodiments, the penile stem cells and compositions described herein are injected into the penis in the form of a spray. In some embodiments, the penile stem cells and compositions described herein are formulated and administered for extended release (e.g., in the form of dissolvable capsules or pellets).

In some embodiments, the penile stem cells are isolated, the stem cells are expanded and then administered to the subject. In the penile stem cells are isolated, formulated for long-term storage (e.g., by freezing) for use at a later date.

In an embodiment, ADRCs are isolated from adipose tissue by triplicate washing in 0.1 mol/L phosphate-buffered saline (PBS), pH=7.4. Tissue is then minced and digested in 0.1% collagenase type I at 37 degrees Celsius for 45 minutes. Afterwards, the solution is filtered and centrifuged at 800 g for eight minutes. Supernatant is removed and cells are resuspended in Modified Eagle's Medium (MEM) supplemented with 10% fetal bovine serum (PBS). Cells are then plated and incubated at 37 degrees Celsius.

ADRCs are harvested from the growth by flow cytometry according to traditional flow cytometry methods, for example as disclosed in Alexander C M et al., Cell Stem Cell 2009; 5: 579-83. Cells are washed in buffer (FBS) and incubated for 30 minutes in FBS with antibodies against CD105, CD90, CD34, and/or CD45. The ADRCs are then combined with adipose cells in a composition for injection.

In embodiments, the ADRCs are processed by washing in PBS followed by ECM digestion in 0.075% collagenase for 30 minutes at 37 degrees Celsius. Digestion is neutralized using Dulbecco's Modified Eagle Medium (DMEM) containing 10% FBS. Digested tissue is then centrifuged at 1200 g for 10 minutes to obtain a cell pellet. The pellet is then resuspended and filtered, and cells are plated. Cell media is removed 12-18 hours later and fresh media provided. Cells are incubated on ice with antibodies to human CD11b, CD18, CD31, CD34, CD38, CD44, CD45, CD54, CD62L, CD90, CD105, CD106, CD117, CD133, CD 144, CD 166, and/or CD271. Cells are then washed and flow cytometry, for example fluorescence-activated cell sorting, is performed according to traditional, known methods, for example as disclosed in Alexander C M et al, Cell Stem Cell 2009; 5:579-83.

In embodiments, the stem cells used in the present composition includes mesenchymal stem cell isolated from bone marrow. In certain preferred embodiments, the bone marrow is that of the patient in need of treatment for a penile defect. Such stem cells may be isolated in accordance with the following protocol, which is to be considered exemplary.

Bone marrow tissue may be obtained from the head of the femur, by transversally segmenting the femoral head to expose trabecular, or cancellous, bone. This trabecular bone may be extracted with successive, serial washes of phosphate-buffered saline (PBS). The solution of PBS and trabecular bone may then be filtered through a filter of any suitable pore diameter, for example and without limitation a 40, 70, or 100 μm cell strainer. The solution may then be centrifuged at 400 g for 10 minutes to form a pellet of cells, the supernatant aspirated, and the pellet resuspended in media containing DMEM supplemented with 10% FBS and 1% streptomycin or penicillin, or both. Cells may then be cultured, and then washed with PBS to remove non-adherent cells. The obtained cells may be further expanded by repeating the incubation and washing steps until a suitable volume of cells is obtained. Medium may be supplemented with heparin and growth factors, if necessary.

In other embodiments, the stem cells may be obtained from placental tissue. Stem cells from this source may be obtained by any method known to those of skill in the art. In certain embodiments, stem cells may be obtained according to the following procedure. Tissue samples from placental tissue may be washed in PBS plus antibiotic solution (200 U/mL penicillin and/or 200 mg/mL streptomycin). The amnion is separated from chorion through fine dissection. Small pieces of both membranes are minced and subjected to enzymatic digestion to obtain a mesenchymal population of cells. The resulting cells are seeded in 25 cm culture flasks with 5 mL of DMEM with 20% FBS and antibiotics (penicillin 100 U/mL and/or streptomycin 100 mg/mL), and incubated at 37 degrees Celsius. Nonadherent cells are removed with changes of medium (DMEM plus 10% FBS). The obtained cells may be further expanded by repeating the incubation and washing steps until a suitable volume of cells is obtained. Medium may be supplemented with heparin and growth factors, if necessary.

In addition to the protocols described herein, stem cells may be obtained from a suitable commercial source for use in the compositions of the present invention. In embodiments, mesenchymal stem cells from placental tissue provided under the trade name OVATION® by Osiris Therapeutics, Inc. may be used. This product is preferred because it includes components of extracellular matrix (ECM) and growth factors.

In certain embodiments, the composition further comprises other agents. These agents may include compositions designed to assist in reducing inflammation, aiding wound healing, promoting angiogenesis and/or vasculogenesis, and degrading collagen. Agents useful for reducing inflammation include, but are not limited to, anti-inflammatory cytokines such as interleukin-4 (IL-4), IL-6, IL-10, IL-11, and IL-13. Cytokines are cell-signaling molecules, which may be categorized as peptides, proteins, or glycoproteins. IL-1 receptor antagonists (IL-IRa) may also be included in the composition to reduce inflammation in the area of treatment. In certain embodiments, the anti-inflammatory agents may include free radical scavengers or antioxidants such as, without limitation, glutathione, selenium, vitamin E, vitamin C, and/or beta-carotene.

Agents useful for enhancing wound healing that may be included with the composition of the present invention include, but are not limited to, growth factors, collagenases, fullerenes and derivatives thereof, pseudopterosin-based compounds, histatin, anti-fibrotic compounds such as tumor growth factor-beta inhibitors, analgesics, and the like. In preferred, embodiments, the agent useful for wound healing is fibroblast growth factor (FGF).

Agents useful for enhancing angiogenesis and/or vasculogenesis that may be included with a composition of the present invention include, but are not limited to, growth factors, matrix mealloproteinases (MMPs), and angiopoietins (Ang1 and Ang2). The growth factors useful in the present composition include the vascular endothelial growth factor (VEGF) family including VEGF-A, VEGF-B, VEGF-C, VEGF-D, and placental growth factor (PGF), and the FGF family (FGF-1 and FGF-2). In certain preferred embodiments, the agent useful for enhancing angiogenesis and/or vasculogenesis is selected from the VEGF family.

The pH a composition of the present invention is preferably from about 6.4 to about 8.3, optimally 7.4. To achieve a desired pH, art-known pH buffer solutions, such as sodium phosphate or bicarbonate, may be used. Excipients may be used to bring the solution to isotonicity, such as, sodium chloride. Other pharmaceutically acceptable agents can also be used to bring the composition to isotonicity, for example, dextrose, propylene glycol, polyols (e.g., mannitol and sorbitol) or other solutes, including basic solutes or acidic solutes in the penis.

As Peyronie's disease is known to result from disorganized collagen, in certain preferred embodiments it is also useful to include a collagenase in the composition, to aid in the breaking down of disorganized collagen in the plaques associated with the disease. Collagenases are enzymes that break the peptide bonds in collagen and aid in breaking down the protein. Collagenases useful in the composition of the present invention may include MMPs and collagenase clostridial histolyticum (available from Auxilium Pharmaceuticals under the trade name XIAFLEX®).

The composition of the present invention may further include a biologic matrix or growth scaffold on which the adipose tissue and stem cells are present. In some embodiments the matrix is a degradable matrix, such that after implantation, the matrix is slowly dissolved by the body's natural processes. Such a scaffold may include collagen fibers or bundles, for example the Three Dimensional Collagen Composite Scaffold available from Becton, Dickinson and Company. Other scaffolds may be formed from isolated components of ECM, or whole ECM. Such scaffolds are available, for example, from Kensey Nash under the trade name MESO BIOMATRIX™ and include porcine mesothelial ECM. Without wishing to be bound by theory, by administering activated stem cells with normal collagen, the stem cells are then able to discriminate between normal and abnormal collagen and create new normal collagen and repair old collagen, in Peyronie's plaques, vascular fibrosis, and allow normal angiogenesis with normal blood vessels being created. Also the growth factors of amnion reactivate the penis's own stem cells allowing them to restore vasculogenesis and digest Peyronie's plaques.

In addition, scaffolds made from synthetic materials may also be used in the composition of the present invention. These scaffolds may be provided by any known process familiar to those in the polymer arts. The synthetic scaffold may include a fabric that can be attached to the site of interest by sutures or the like, or a may be held in place by an adhesive that is acceptable for use in humans. Such scaffolds can be formed into any suitable shape.

In a preferred, embodiment, the composition is provided on an ECM scaffold. The ECM may be obtained from any commercial source. The ECM scaffold may be biodegradable or not, but preferably is biodegradable. In such an embodiment, the adipose tissue and at least one isolated stem cell may be disposed on the surface of the scaffold, or may be embedded within a three-dimensional scaffold. Formation of such scaffolds, through dissociation of tissue, digestion, lyophilization, and reconstitution, may be accomplished by any procedure known to those of skill in the art.

In some embodiments, the scaffold is a fibrin scaffold that is injectable, for example through the method also provided herein. Injectable fibrin scaffolds are known in the art, for example, a group has seen growth of cardiac cells following implantation of ADRCs on a fibrin scaffold via injection. Zhang et al, Preservation of the cardiac function in infracted rat hearts by the transplantation of adipose-derived stem cells with injectable fibrin scaffolds. Exper. Biol. & Med. 2010; 235: 1505-1515.

Another aspect of the current invention provides for a method of treating an individual having a penile defect. The method comprises providing a composition of at least one isolated stem cell, and implanting the composition within the penis of the individual. The method may be used for treatment of erectile dysfunction (ED) and Peyronie's disease, among other defects or disorders.

In an embodiment, the implanting step comprises providing a biological scaffold or matrix comprising the composition. Examples of suitable biological scaffolds are known to those skilled in the art. In some embodiments the matrix is a degradable matrix, such that after implantation, the matrix is slowly dissolved by the body's natural processes.

In a further preferred embodiment, the composition is provided on an ECM scaffold, for example, from Kensey Nash under the trade name MESO BIOMATRIX™, and that scaffolding is then implanted into the subject. The ECM scaffold may be biodegradable or not.

In yet another embodiment, the composition is implanted into a subject by injection. The pellet of cells obtained by the method provided herein is resuspended in a suitable solution and injected into appropriate areas of the body.

In preferred embodiments, the implantation is directed toward the subject's penis. Implantation into the penis may be at any suitable location or anatomy for addressing the particular defect. Implantation may be of the composition, including in some embodiments adipose tissue and/or a scaffold or matrix, by injection of a solution, or by any other method known for introducing stem cells to a target. In embodiments, injection occurs at the target site and is in at least 50 micro liter volumes delivered in a needle of suitable gauge for the anatomy.

In further preferred, embodiments, the implantation is directed towards at least one of the subject's corpora cavernosa. In preferred, embodiments, a solution comprising the composition of isolated stem cells is injected directly into or around at least one of the corpora cavernosa. In preferred, embodiments, a solution comprising the composition of isolated stem cells, specifically isolated penile stem cells isolated as described above or Penis Platelet Rich Plasma, is injected directly into scar tissue present on the penis or into the corpora cavernosum of an individual with Peyronie's disease. In additional embodiments, the composition is injected or infused into any artery that feeds penile tissue. In certain embodiments, the composition is injected or infused into the corporal arteries or internal pudendal arteries.

In another embodiment, the composition is implanted into or around the subject's tunica albuginea. Stem cells, such as ADRCs in a embodiment, stimulate the growth of human tissues. Wounded tissue is most often replaced by scar tissue, such as that present in Peyronie's disease. This scar tissue is characterized in the skin by disorganized collagen structure and irregular vascular structure. Stem cells reorganize collagen and induce vasculogenesis, aiding in wound healing, such as in wounds present in Peyronie's disease.

Proliferation and/or differentiation of cells may be accomplished before or after transplantation, and in various combinations of in vitro or in vivo conditions, including (1) proliferation and differentiation in vitro, then transplantation, (2) proliferation in vitro, transplantation, then further proliferation and differentiation in vivo, and (3) proliferation in vitro, transplantation and differentiation in vivo. Those skilled in the art can follow standard methodology to transform the stem cells of the current invention into a desired cell type or engineered construct for use in implantation for the purposes described herein. The penile stem cells may be activated by known methods in the art, such as centrifugation, vibration, shock waves, or light.

While treatment of Peyronie's disease and erectile dysfunction is discussed in detail below, the penile stem cells and compositions described herein can be used for other penile defects, such as urethral stricture disease and fistula and hypospadias repair and incontinence bulking surgery or trauma from injury—scar from fracture or priapism or trauma or in emergency room setting in a priapism case.

Treatment of Peyronie's Disease (PD)

A composition of the present invention is administered to subjects having Peyronie's disease (PD). Peyronie's disease is an ailment involving the growth of fibrous scar tissue, or plaques, in the soft tissue of the penis, which results in abnormal bending of the organ. The etiology of the plaques is not known. These plaques grow in the tunica albuginea, a region of connective tissue that is part of the more general connective tissue of Buck's fascia. The tunica albuginea is an area surrounding the corpora cavernosa. The disease results in pain, erectile dysfunction (ED), and alteration of penis shape, and may be caused by disorganized collagen fibers. Treatments for the disease currently include administration of corticosteroids to the plaques, radiation therapy, and vitamin E. Pharmaceuticals for treatment exist; however, the use of medicaments is considered controversial.

Prior to administration of a composition of the present invention, baseline measurements are taken to assess the state of health of the subjects. These assessments include the following:

Subjects will have peak penile artery velocity in the corporal arteries measured with penile doppler and ultrasound. Penile doppler is a standard tool for the evaluation of ED, and is less invasive than typical means for measuring artery velocity, angiography with selective internal iliac angiography. Penile Doppler may be performed with a high frequency transducer (7.5-9.0 MHz), and at least the inner diameter of the cavernosal artery, baseline peak systolic velocity, and end diastolic velocity are measured. A normal value for inner diameter of the cavernosal artery is 0.3-0.5 mm. In a flaccid state, monophasic flow should be seen in an individual without Peyronie's disease. In an erect state, a velocity of greater than 30 cm/sec should be observed in an individual without ED, which is often a symptom of Peyronie's disease.

In addition to penile artery velocity, the size of fibrous plaques present on the penis is also assessed prior to the initiation of any treatment. This may be done with ultrasound, at which time the grade of Peyronie's may be assigned to the subject. Peyronie's grades are given according to the following: Grade 1 (plaque less than 0.3 cm), Grade 2 (greater than 0.3 cm and less than 1.5 cm), and Grade 3 (greater than 1.5 cm, or two plaques greater than 1 cm).

Angle of penile curvature, a hallmark of Peyronie's disease, is also measured prior to initiation of treatment. Curvature may be assigned a grade according to the following, based on the Kelami classification system: Grade 1 (curvature of 30 degrees or less), Grade 2 (curvature of 30 degrees to 60 degrees), and Grade 3 (curvature of greater than 60 degrees).

A penile rigidity test is also performed prior to initiation of treatment. This test may be done as a nocturnal penile tumescence (NPT test) or an intracavernosal injection test. In an NPT test, the frequency and quality of an erection during sleep is assessed by either placing a ring-like device around the subject's penis, or by use of an electronic monitoring device. The ring-like device is a simple mechanical device consisting of plastic films, which shear at certain pressures, for example when an erection provides sufficient pressure on the ring to break the film. The electronic measurement includes a device that measures frequency, temporal length, and rigidity of erections during sleep. This is a preferred means for measuring rigidity. These variations of the NPT test may be conducted in a polysomnography or other sleep lab, or at the subject's home. The NPT test is usually performed over two consecutive nights for accuracy.

Another form of rigidity test, the intracavernosal injection test, involves injection of alprostodil (a formulation of prostaglandin E1 available under the trade names EDEX® from actient pharmaceuticals and CAVERJECT® from Pfizer) or Tri-Mix (a mixture of Prostaglandin E1, Phentolamine, and Papaverine) into the base of the penis, which causes an erection through its vasodilator properties. Following the injection, fullness and length of the erection are measured. The test may be repeated as necessary for increased accuracy. The length and circumference of each subject's penis is also assessed prior to treatment.

Subjects are also given the International Index of Erectile Function (IIEF) Questionnaire prior to initiation of treatment. This questionnaire asks subjects to rate various parameters relating to ED by answering fifteen questions, and assigns point values from zero to five to each answer. A score of 25-30 indicates no ED, and a score of 0-6 indicates severe ED. A continuum of moderate to mild ED exists between a score of 7 and 24. A shortened version of the IIEF, the IIEF-5 may be administered. In this short form, five questions are to be answered, and a score of 22-25 means that the subject does not have ED, and a score of 5-7 means the subject has severe ED. A continuum of moderate to mild ED exists between a score of 7 and 22.

Following baseline measurements of the above variables, a composition including stem cells, preferably penile stem cells, is administered to the subject by implantation in the penis. This implantation is by surgical incision and implantation with a biodegradable scaffold having stem cells present therein, by injection of the composition on an injectable fibrin scaffold, or injection of the stem cells alone, or with an injectable fibrin scaffold. Various groups including other elements such as growth factors, anti-inflammatories, antioxidants, and collagenases are included. Injections are made into the tunica albuginea surrounding the corpora cavernosa and/or the corpora cavernosa themselves, any artery feeding penile tissue, or the corporal arteries or internal pudendal arteries. Repeated injections may be necessary.

Following administration of the composition, follow-up observations, including each of the aforementioned variables (arterial velocity, penile plaque size, penile curvature, IIEF score, and rigidity testing) are collected at three months, six months, and twelve months. Increased velocity, decreased plaque size, decreased curvature, increased IIEF score, and increased rigidity are expected. Shortening of time for improvement is expected in those receiving collagenase as well.

Treatment of Erectile Dysfunction (ED)

A composition of the present invention is administered to subjects having erectile dysfunction (ED). ED is an ailment in which a male is unable to achieve or sustain an erection suitable for sexual intercourse. A number of factors are believed to play a role in or be directly responsible for ED, including obesity, blood pressure, chronic illnesses such as diabetes, poor blood flow to the penis, smoking tobacco, alcoholism, and side-effects of other medications.

Treatments for ED currently include cessation of potential causes such as smoking tobacco and consumption of alcohol, hormone (testosterone) replacement, surgery, and administration of pharmaceuticals such as vardenafil, tadalafil, and sildenafil. Some of these pharmaceuticals are controversial for their incompatibility with nitrate drugs, and for their unwanted side-effects, such as effects on vision (blurring, loss of vision) and priapism.

Prior to administration of a composition of the present invention, baseline measurements are taken to assess the state of health of the subjects. These assessments include the following:

Subjects will have peak penile artery velocity in the corporal arteries measured with penile doppler and ultrasound, as discussed above. In a flaccid state, monophasic flow should be seen. In an erect state, a velocity of greater than 30 cm/sec should be observed in an individual without ED.

A penile rigidity test is also performed prior to any initiation of treatment. This test may be done as a nocturnal penile tumescence (NPT test) or an intracavernosal injection test, as discussed above. Another form of the rigidity test is the intracavernosal injection test, which as discussed above, involves injection of alprostadil (a formulation of prostaglandin E) available under the trade names EDEX® from actient pharmaceuticals and CAVERJECT® from Pfizer) or Tri-Mix (a mixture of Prostaglandin E1, Phentolamine, and Papaverine) into the base of the penis causing an erection. Following the injection, fullness and length of the erection are measured. The length and circumference of each subject's penis is also assessed prior to treatment.

As discussed above, subjects are also given the International Index of Erectile Function (IIEF) Questionnaire—or shortened version of the IIEF, the IIEF-5—prior to initiation of treatment.

Following baseline measurements of the above variables, a composition including stem cells, preferably penile stem cells, is administered to the subject by implantation in the penis. This implantation is by surgical incision and implantation with a biodegradable scaffold having stem cells present therein, by injection of the composition on an injectable fibrin scaffold, or injection of adipose tissue and stem cell alone. Various groups including other elements such as growth factors, anti-inflammatories, antioxidants, and collagenases are included. Injections are made into the tunica albuginea surrounding the corpora cavernosa and/or the corpora cavernosa themselves, any artery feeding penile tissue, or the corporal arteries or internal pudendal arteries. Repeated injections may be necessary.

Following administration of the composition, follow-up observations, including each of the aforementioned variables (arterial velocity, rigidity testing, and IIEF score) are collected at three months, six months, and twelve months. Increased velocity, increased IIEF score, and increased rigidity are expected.

EXAMPLES

Treatment of Peyronie's Disease, Erectile Dysfunction and other Penile Defects with Penile Stem Cells.

Patients with erectile dysfunction (ED), Peyronie's Disease (PD) and penile fibrotic trauma were selected. They were given an artificial erection with Tri-Mix (a mixture of Prostaglandin E1, Phentolamine, and Papaverine), which allows the corpora cavernosum and the cavernosa spaces to fill and be pressurized with blood. The stem cells are believed to live in the crevices of the corpora.

After applying local anesthesia to each patient, a large bore needle was inserted into the corpora cavernosa and aspirated to obtain 60 cc of blood and blood products. The blood and blood products, were centrifuged (e.g., in a centrifuge used for deriving platelet rich plasma or for separating bone marrow stem cells from the fluid derived from a bone marrow aspiration) to separate the fluid into different cell layers, including a layer of mononuclear cells and platelet rich plasma. The platelet rich plasma layer was extracted and collected, which provided 10 mL of blood product substantially free of red blood cells, which was rich in growth factors and penile stem cells. The mononuclear cell layer was also extracted since it is expected to have penile stem cells.

This fluid containing the penile stem cells had a cell count of ~106 mononuclear cells, which is 2-5 times greater than normal plasma. The cells were plated and grown. Stem cells were found to be present in a higher concentration then is found in typical blood. Flow cytometry was performed to further characterize the penile stem cells (See Table 1).

TABLE 1

| | TNC/mL | CFU-F Frequency | CFU-F per ml | CD34+ % | CD34+ cells/mL | CD146+ % | CD146+ cell/mL |
|---|---|---|---|---|---|---|---|
| 12/22 - Sample 1 | $9.55 \times 10^6$ | 0 | 0 | No data | No data | No data | No data |
| 12/22 - Sample 2 | $11.3 \times 10^6$ | 1/250,000 | 45 | No data | No data | No data | No data |
| 12/22 - Sample 3 | X | X | X | X | X | X | X |
| 2/6 - BM 1 | $20.6 \times 10^6$ | 1/250,000 | 82.6 | 8.09% | $3.06 \times 10^5$ | 1.51% | $31.2 \times 10^4$ |
| 2/6 - Penis PRP 1 | $8.75 \times 10^6$ | 0 | 0 | 6.16% | $5.39 \times 10^5$ | 0.57% | $4.99 \times 10^4$ |
| 2/6 - Penis PRP 2 | $5.56 \times 10^6$ | 0 | 0 | 6.52% | $3.63 \times 10^5$ | 1.05% | $5.84 \times 10^4$ |
| 4/17 - Penis PRP 1 | $36.5 \times 10^6$ | TBD | TBD | X | X | X | X |
| 4/17 - Penis PRP 2 | $18.9 \times 10^6$ | TBD | TBD | X | X | X | X |
| 4/17 - Penis PRP 3 | $10.3 \times 10^6$ | TBD | TBD | X | X | X | X |
| Typical Whole Blood | 800K - 4 million | 0 | 0 | 1-4% | $10^5$-$10^5$ | Not in literature | Not in literature |
| Typical PRP | 5-20 million | 0 | 0 | 2-7% | $10^5$-$10^5$ | Not in literature | Not in literature |
| Typical BMA | 1-10 million | 1/75,000 | 100-1000/mL | 3-8% | $10^5$-$10^5$ | Not in literature | Not in literature |
| Typical BMC | 20-100 million | 1/50,000 | 1000-5000/mL | 4-12% | $10^6$-$10^7$ | Not in literature | Not in literature |

TABLE 1-continued

Collagenase Digested Biopsy Tissue

| | TNC per punch | CFU-F Freq. | CFU-F per punch | CD34+ % | CD34+ cells/mL | CD146+ % | CD146+ cell/mL |
|---|---|---|---|---|---|---|---|
| 2/6 -Tissue Biopsy 4 punches | 6.75 × 10$^4$ | 1/30,000 | 2.3 | Not enough cells | Not enough cells | Not enough cells | Not enough cells |
| 4/17 Patient 1 Tissue | All Punches 2.36 × 10$^5$ | TBD | TBD | Not enough cells | Not enough cells | Not enough cells | Not enough cells |
| 4/17 Patient 3 Tissue | All Punches 2.8 × 10$^5$ | TBD | TBD | Not enough cells | Not enough cells | Not enough cells | Not enough cells |

Each patient was given an artificial erection. The fluid containing the penile stem cells was injected back into the erect penis of the patient from which it was derived. Since the patient had an artificial erection the cellular material was able to stay in the penis without the need for a penile clamp to keep the fluid in. If the penis had gone flaccid, a penile ring or clamp could have been used to keep the fluid in.

For the erectile dysfunction patient, the fluid was evenly injected into both corpora cavernosum.

For the Peyronie's Disease patient, the fluid was injected into both corpora and around and in all of the penile plaques and abnormal areas of the tunica albuginea.

For the penile trauma patient and/or patient with Priapism, the fluid is injected it in both corpora and in the fibrotic areas.

The patients were examined at two and three weeks after the procedure. The patients showed much improvement with them getting erections more often. Furthermore, the Peyronie's Disease patient no longer had pain associated with erections; the fibrotic trauma patient had a softer penis.

In a patient with an active priapism, the priapism is drained the same technique of centrifuging and reinjecting the cells is performed.

While the present invention has been described in connection with the preferred embodiments, it is to be understood that other similar embodiments may be used or modifications and additions may be made to the described embodiments for performing the same function of the present invention without deviating therefrom. Therefore, the present invention should not be limited to any single embodiment, but rather construed in breadth and scope in accordance with the recitation of the appended claims.

What is claimed is:

1. A composition comprising: a mixture of a population of isolated penile stem cells free of red blood cells mixed with amnion and/or amniotic fluid, the mixture having a pH from 6.46 to 8.3 achieved by the addition of buffer solutions or excipients to bring the solution to isotonicity including sodium phosphate, sodium chloride, bicarbonate, or pharmaceutically acceptable agents, and the mixture further having one or more of testosterone, human chorionic gonadotropin (hCG), human growth hormone (HGH), somatropin or a combination thereof; at least one extracellular matrix component, wherein the extracellular matrix component comprises collagen and collagenase, the collagenase being clostridial collagenase, wherein the collagenase breaks down collagen while introducing collagen; and wherein the isolated penile stem cells are obtained from a whole blood specimen taken from a penis of a subject separated from the whole blood into fractions of platelet-rich plasma (PRP) and red blood cells in a first spin, wherein the red blood cells are discarded and the platelet-rich plasma (PRP) is concentrated in a second spin forming a supernatant of platelet poor plasma (PPP) which is removed leaving the platelet-rich plasma (PRP) having the isolated penile stem cells, the isolated penile stem cells being expanded and thereafter mixed with the amnion and/or amniotic fluid to form the composition to which collagenase is added to aid in breaking down disorganized collagen in plaques associated with Peyronie's disease.

2. The composition according to claim 1, further comprising at least one growth factor.

3. The composition according to claim 1, further comprising non-penile stem cells, wherein the non-penile stem cells are pericytes.

4. The composition according to claim 1, wherein the stem cells are derived from tissue from a biopsy of the penis.

5. The composition according to claim 1, wherein the stem cells are derived from a biopsy or blood and is obtained with a spreading needle that decreases the risk of corporal injury.

6. The composition according to claim 1, further comprising a biological scaffolding, wherein the scaffolding is biodegradable and wherein the scaffolding is time-release or viscous.

7. The composition according to claim 1, further comprising at least one additional agent wherein the agent promotes at least one of wound healing, angiogenesis, vasculogenesis, and degradation of collagen.

8. The composition of claim 7, wherein the agent is an anti-inflammatory or an antioxidant.

9. The composition of claim 1, wherein the pH is adjusted to 7.4.

* * * * *